(12) United States Patent
Woodruff et al.

(10) Patent No.: US 9,060,840 B2
(45) Date of Patent: Jun. 23, 2015

(54) NEEDLE TARGETING APPARATUS FOR IMPLANTED DEVICE

(75) Inventors: Scott A. Woodruff, Cincinnati, OH (US); Amy L. Marcotte, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 925 days.

(21) Appl. No.: 12/639,594

(22) Filed: Dec. 16, 2009

(65) Prior Publication Data

US 2011/0144597 A1 Jun. 16, 2011

(51) Int. Cl.
*A61F 5/00* (2006.01)
*A61B 17/34* (2006.01)
*A61M 39/02* (2006.01)
A61B 19/00 (2006.01)
A61M 39/00 (2006.01)

(52) U.S. Cl.
CPC ........... *A61F 5/0056* (2013.01); *A61B 17/3403* (2013.01); *A61B 2019/4836* (2013.01); *A61M 39/0208* (2013.01); *A61M 2039/0081* (2013.01); *A61M 2039/0238* (2013.01)

(58) Field of Classification Search
CPC . A61M 5/425; A61M 5/427; A61M 39/0208; A61M 2205/6081; A61M 5/14276; A61B 2019/5255
USPC ............................................. 604/116, 890.1
See application file for complete search history.

(56) References Cited

U.S. PATENT DOCUMENTS

| | | | |
|---|---|---|---|
| 5,171,228 A | 12/1992 | McDonald | |
| 5,620,419 A * | 4/1997 | Lui et al. | 604/116 |
| 5,773,721 A * | 6/1998 | Bashyam | 73/596 |
| 6,067,991 A | 5/2000 | Forsell | |
| 6,423,076 B1 | 7/2002 | Cardwell et al. | |
| 6,461,292 B1 | 10/2002 | Forsell | |
| 6,470,892 B1 | 10/2002 | Forsell | |
| 7,169,155 B2 * | 1/2007 | Chu et al. | 606/130 |
| 7,416,528 B2 | 8/2008 | Crawford et al. | |
| 7,442,165 B2 | 10/2008 | Forsell | |
| 7,621,863 B2 | 11/2009 | Forsell | |

(Continued)

FOREIGN PATENT DOCUMENTS

WO WO 99/38438 8/1999

OTHER PUBLICATIONS

International Search Report dated Mar. 22, 2011 for Application No. PCT/US2010/059133.

*Primary Examiner* — Edelmira Bosques
(74) *Attorney, Agent, or Firm* — Frost Brown Todd LLC

(57) ABSTRACT

A needle targeting apparatus comprises a sense head configured to locate an implanted device and a guide. The guide is associated with the sense head and comprises an upper surface, a lower surface, and a support member. The support member comprises a channel extending through the support member that provides access to an injection site. In some versions, a needle targeting apparatus comprises a locating feature, an alignment feature, and a support feature. The locating feature is configured to locate an implanted device. The alignment feature is configured to align a syringe needle with the implanted device. The support feature is configured to support a syringe upon insertion of the syringe needle into the implanted device. In some versions, a needle targeting apparatus comprises a sense head configured to locate an implanted device and a guide. The guide is configured to identify the center of the sense head.

11 Claims, 15 Drawing Sheets

(56) References Cited

U.S. PATENT DOCUMENTS

| | | | |
|---|---|---|---|
| 8,573,228 B2* | 11/2013 | Kalpin | ........................ 128/899 |
| 2003/0114862 A1 | 6/2003 | Chu et al. | |
| 2006/0211914 A1 | 9/2006 | Hassler, Jr. et al. | |
| 2008/0250340 A1 | 10/2008 | Dlugos, Jr. et al. | |
| 2009/0234302 A1 | 9/2009 | Hoendervoogt et al. | |

* cited by examiner

NEEDLE TARGETING APPARATUS FOR IMPLANTED DEVICE

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006 (now U.S. Pat. No. 7,775,215), the disclosure of which is incorporated by reference herein.

While a variety of gastric band systems and associated components have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
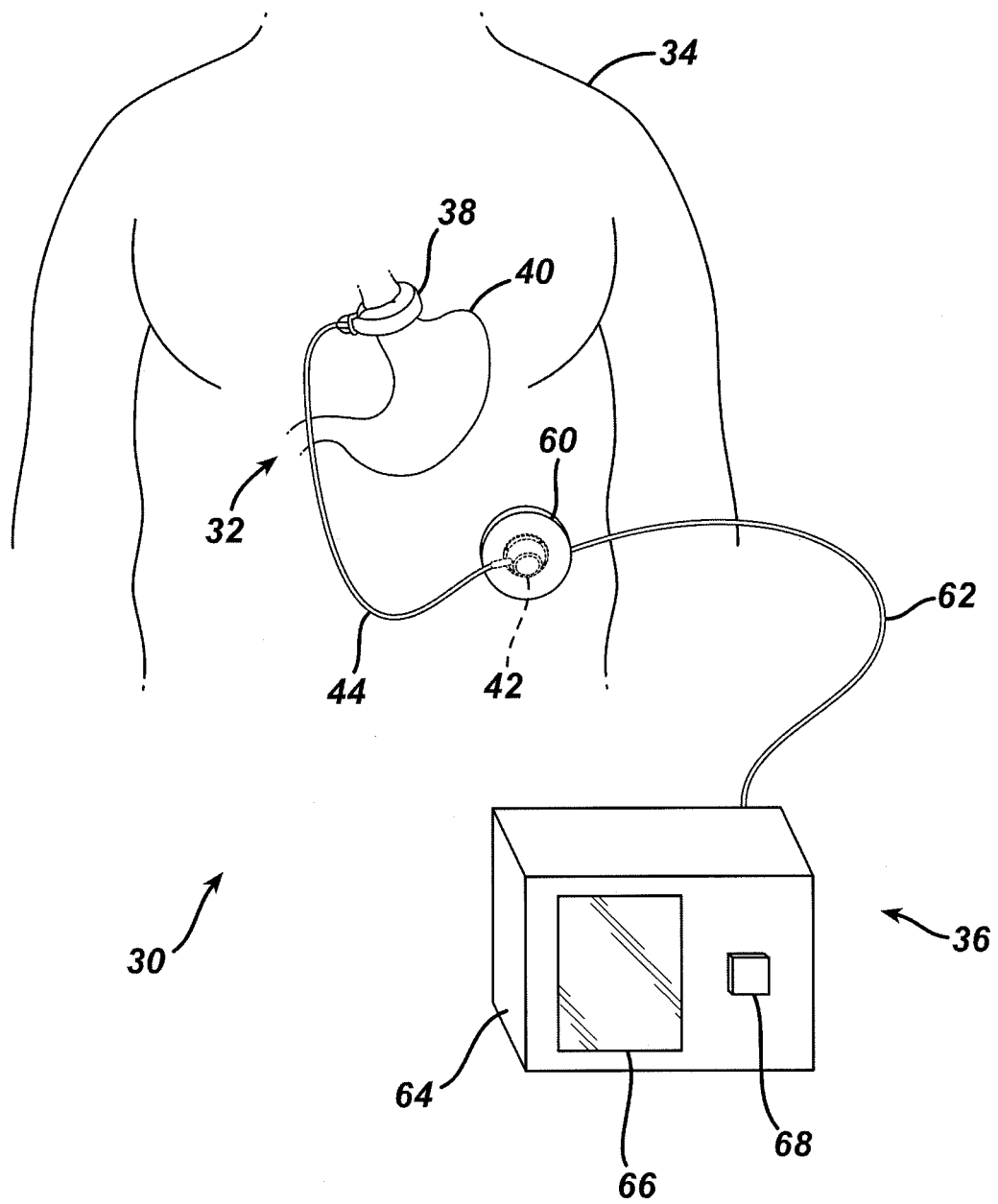
FIG. 1 depicts a schematic illustration of an exemplary food intake restriction device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Referring now to the drawings in detail, wherein like numerals indicate the same elements throughout the views, FIG. 1 illustrates an exemplary food intake restriction system 30. System 30 comprises a first portion, identified generally as 32, implanted inside of a patient 34; and a second portion, identified generally as 36, located external to the patient. Implanted portion 32 comprises an adjustable gastric band 38 positioned on the upper portion of the patient's stomach 40. Adjustable band 38 may include a cavity or bladder made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. An injection port 42, which will be described in greater detail below, is implanted in a body region accessible for needle injections and/or telemetry communication signals. In the example shown, injection port 42 fluidly communicates with adjustable band 38 via a catheter 44. A surgeon may position and permanently implant injection port 42 inside the body of the patient in order to perform adjustments of the food intake restriction or stoma. The surgeon, for example, may implant injection port 42 in the lateral, subcostal region of the patient's abdomen under the skin and layers of fatty tissue. The surgeon may alternatively implant injection port 42 on the sternum of the patient or in any other suitable location.

Figure 2:
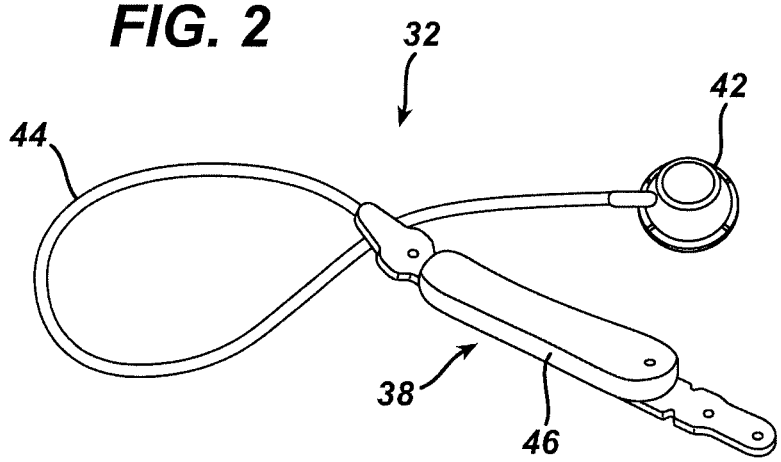
FIG. 2 depicts a more detailed perspective view of an exemplary implantable portion for the food intake restriction device of FIG. 1.

FIG. 2 illustrates an exemplary adjustable gastric band in greater detail. In this example, band 38 includes a variable volume cavity 46 that expands or contracts against the outer wall of the stomach to form an adjustable stoma for controllably restricting food intake into the stomach. A physician may decrease the size of the stoma opening by adding fluid to variable volume cavity 46 or, alternatively, may increase the stoma size by withdrawing fluid from the cavity. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
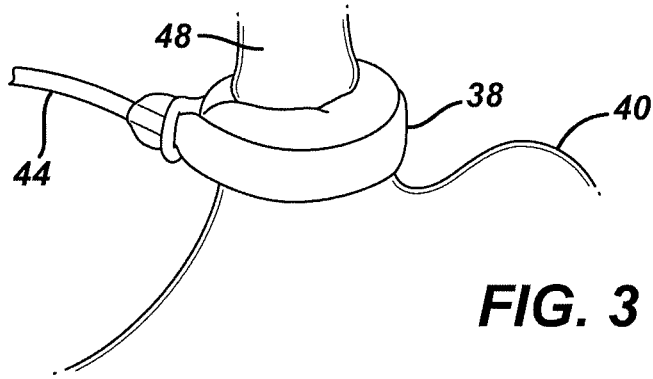
FIG. 3 depicts a perspective view of the adjustable gastric band of FIG. 2, showing the band positioned around the gastro-esophageal junction of a patient.
Figure 4:
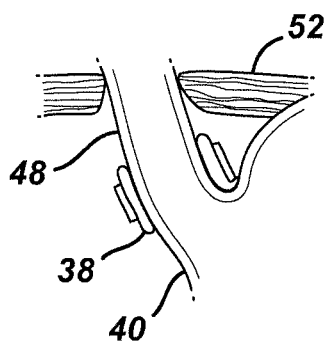
FIG. 4 depicts a cross-sectional view of the adjustable gastric band of FIG. 2, shown in a deflated configuration.
Figure 5:
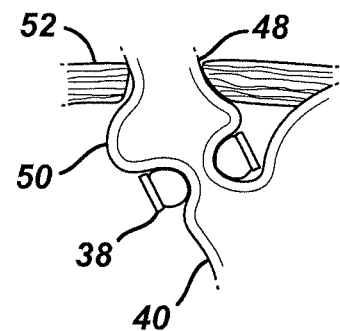
FIG. 5 depicts a cross-sectional view of the adjustable gastric band of FIG. 2, shown in an inflated configuration to create a food intake restriction.

FIG. 3 shows the adjustable gastric band 38 of FIG. 2 applied about the gastro-esophageal junction of a patient. As shown in FIG. 3, band 38 at least substantially encloses the upper portion of stomach 40 near the junction with esophagus 48. FIG. 4 is a sectional view of band 38, showing the band in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within the band 38, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises an external monitoring device 60 electrically connected (in this embodiment via an electrical cable assembly 62) to a control box 64. In an alternate embodiment (not shown), monitoring device 60 may be wirelessly connected to control box 64. Control box 64 includes a display 66, one or more control switches 68, and, in some embodiments, an external control module, which will be explained in further detail below. In alternate embodiments, at least a portion of external control module may be incorporated within monitoring device 60. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or monitoring device 60 to facilitate cleaning, maintenance, usage, and storage of external portion 36 of system 30. Control box 64 may comprise a conventional desktop computer, a laptop computer, a portable electronic device (e.g., BlackBerry, iPhone, etc.), a customized/dedicated device, or any other suitable type of device, including combinations thereof.

Monitoring device 60 may be configured to communicate with implanted portion 32, specifically port 42, as described in more detail below. Such communication may allow monitoring device 60 to locate port 42 and non-invasively receive measurements of the pressure of the fluid within implanted portion 32 even when injection port 42 is implanted beneath thick (e.g., at least over 10 centimeters) subcutaneous fat tissue. In some versions, monitoring device 60 may be configured to either locate port 42 or measure the pressure of the fluid within implanted portion 32, to both locate port 42 and measure the pressure of the fluid within implanted portion 32, or to accomplish one or both of those functionalities in conjunction with additional functionalities related to communication between monitoring device 60 and implanted portion 32. By way of example only, monitoring device 60 may comprise any suitable device, including but not limited to sense head 200, 300, 400, 500, 600 described below. The physician may hold monitoring device 60 near or against the patient's skin near the location of injection port 42 in the patient and observe the pressure reading on display 66 of control box 64. Monitoring device 60 may also be removably attached to the patient, such as during a prolonged examination, using straps, adhesives, and/or using any other suitable components, features, devices, and/or techniques. Monitoring device 60 may operate through conventional cloth or paper surgical drapes, and may also include a disposal cover (not shown) that may be replaced for each patient.

Figure 6:
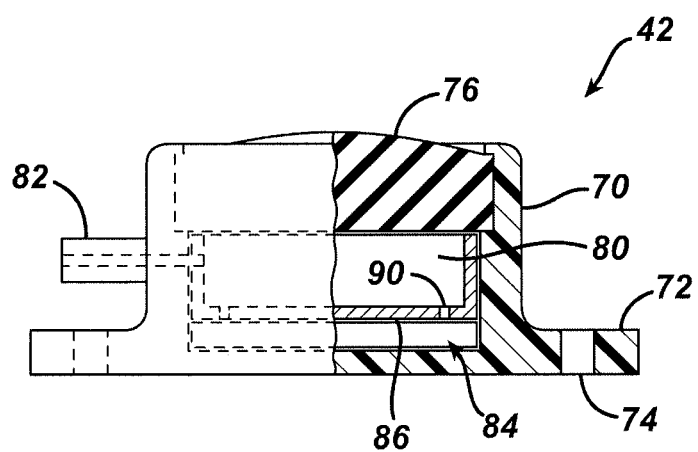
FIG. 6 depicts a side, partially cross-sectioned view of the injection port shown in FIG. 2.

FIG. 6 depicts a side, partially sectioned view of injection port 42 containing a pressure sensing system for non-invasively measuring the fluid pressure within implanted portion 32. As shown in FIG. 6, injection port 42 comprises a rigid housing 70 having an annular flange 72 containing a plurality of attachment holes 74 for fastening the injection port to tissue in a patient. A surgeon may attach injection port 42 to the tissue, such as the fascia covering an abdominal muscle, using any one of numerous surgical fasteners including suture filaments, staples, and clips. In some versions, injection port 42 has integral fasteners that are selectively extendable to secure injection port 42 within the patient. For instance, injection port 42 may be configured in accordance with at least some of the teachings of U.S. Pub. No. 2005/0283118, entitled "Implantable Medical Device with Simultaneous Attachment Mechanism and Method," published Dec. 22, 2005 (now U.S. Pat. No. 7,850,660), the disclosure of which is incorporated by reference herein. Alternatively, injection port 42 may have any other suitable configuration and/or operability.

Injection port 42 of the present example further comprises a septum 76. Septum 76 may be made of a silicone rubber and compressively retained in housing 70. Alternatively, septum 76 may be formed of any other suitable material(s) and/or may be retained in housing 70 in any other suitable fashion. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 42. Injection port 42 further comprises a reservoir 80 for retaining a working fluid (e.g., saline) and a catheter connector 82. Connector 82 attaches to catheter 44, shown in FIG. 2, to form a closed hydraulic circuit between reservoir 80 inside of injection port 42 and cavity 46 within adjustable band 38. Fluid from reservoir 80 may be used to expand the volume of band cavity 46. Alternatively, fluid may be removed from cavity 46 and retained in reservoir 80 in order to temporarily decrease the volume of cavity 46. Housing 70 and connector 82 may be integrally molded from a biocompatible polymer or constructed from a metal such as titanium or stainless steel. Of course, various other configurations and versions for a port 42 will be apparent to those of ordinary skill in the art in view of the teachings herein.

A pressure sensing system is provided in injection port 42 to measure the fluid pressure within the closed hydraulic circuit of implanted portion 32. The pressure within the circuit may correspond to the degree of restriction applied by adjustable band 38 to the patient's stomach 40. Accordingly, measuring the fluid pressure may enable a physician to evaluate the restriction created by a band adjustment. Fluid pressure may be measured before, during, and/or after an adjustment to verify that the band is properly adjusted. In the example shown in FIG. 6, the pressure sensing system comprises a sensor 84 positioned at the bottom of fluid reservoir 80 within housing 70. A retaining cover 86 extends above pressure sensor 84 to substantially separate the sensor surface from reservoir 80, and protect the sensor from needle penetration. Retaining cover 86 may be made of a ceramic material such as, for example, alumina, which resists needle penetration yet does not interfere with electronic communications between pressure sensor 84 and monitoring device 60. Retaining cover 86 includes a vent 90 that allows fluid inside of reservoir 80 to flow to and impact upon the surface of pressure sensor 84. Of course, a pressure sensing system in injection port 42 (and/or elsewhere within implanted portion 32) may have a variety of other components and configurations. By way of example only, the above described pressure sensing system may be substituted or supplemented with any of the various types of pressure sensing systems described in U.S. Pub. No. 2006/0211914, entitled "System and Method for Determining Implanted Device Positioning and Obtaining Pressure Data" published Sep. 21, 2006 (now U.S. Pat. No. 7,775,215), the disclosure of which is incorporated by reference herein. Still other suitable components and configurations for an implantable pressure sensing system will be apparent to those of ordinary skill in the art in view of the teachings herein.

Pressure data obtained using pressure sensing components described herein may be processed and presented on display 66 in a variety of ways. In addition, the user may react to such pressure data in a variety of ways. Various suitable ways in which pressure data may be processed, presented, and reacted to are disclosed in U.S. Pub. No. 2008/0250340, entitled "GUI for an Implantable Restriction Device and Data Logger," published Oct. 9, 2008 (now U.S. Pat. No. 8,870,742), the disclosure of which is incorporated by reference herein. Other ways in which pressure data may be processed, presented, and reacted to are disclosed in U.S. Pub. No. 2006/0211914, entitled "System and Method for Determining Implanted Device Positioning and Obtaining Pressure Data," published Sep. 21, 2006 (now U.S. Pat. No. 7,775,215), the disclosure of which is incorporated by reference herein. Still other suitable ways in which pressure data may be processed, presented, and reacted to will be apparent to those of ordinary skill in the art in view of the teachings herein.

Figure 7:
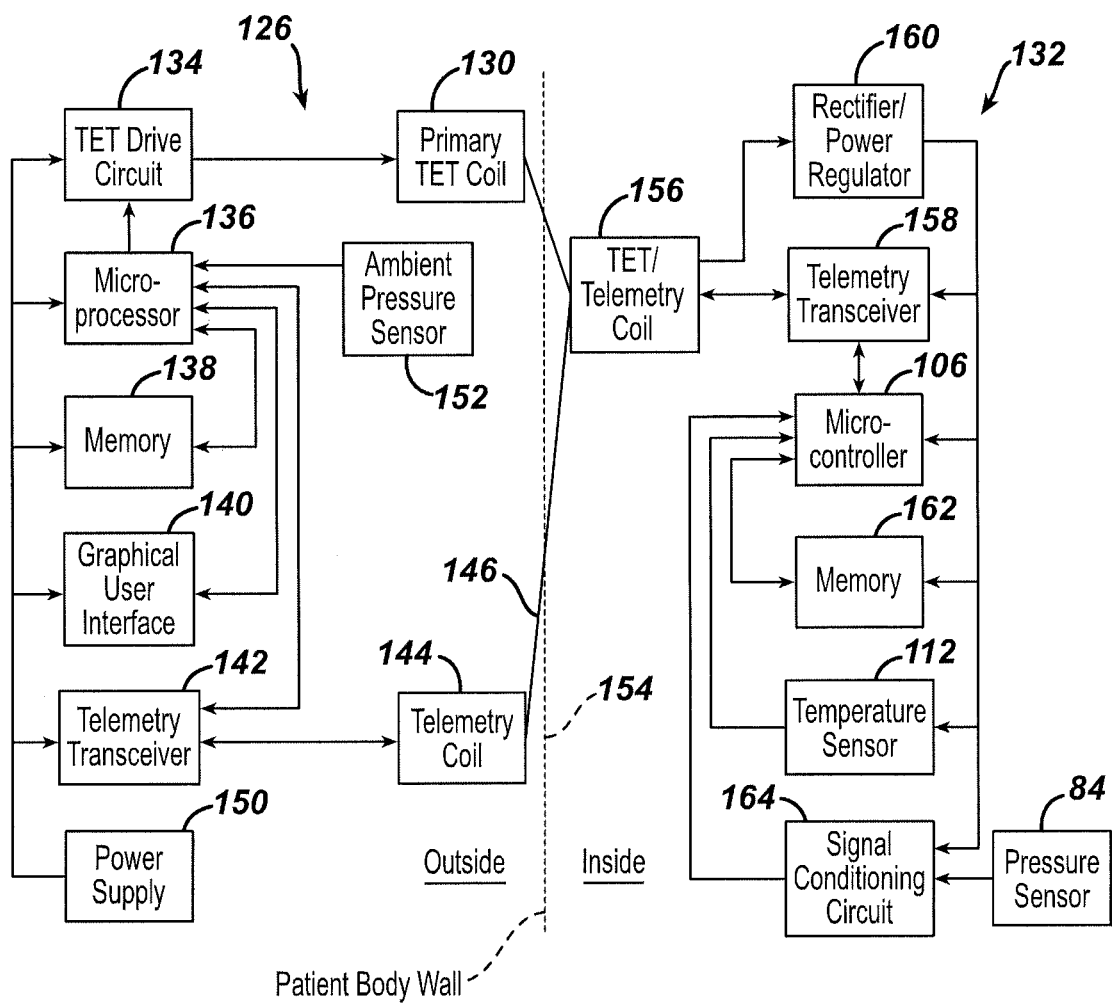
FIG. 7 depicts a block diagram representing an exemplary pressure measurement and location identification system.

Injection port 42 may further comprise an antenna or TET/Telemetry coil configured to both receive power via transcutaneous energy transfer (TET) from an external device and transmit data back to an external device. FIG. 7 is a block diagram of an exemplary pressure measurement and location identification system. As shown in FIG. 7, an external control module 126 of the system includes a primary TET coil 130 for transmitting a power signal to the internal control module, indicated generally as 132. External control module 126 also includes a telemetry coil 144 for receiving data from the internal control module 132. Of course, coils 130, 144 may be combined into a single coil that provides both TET and telemetry functionalities, if desired. The external control module 126 may be at least partially incorporated within an external device, such as monitoring device 60 or sense heads 200, 300, 400, 500, 600 described below and/or control box 64. For instance, primary TET coil 130 and telemetry coil 144 may be located in monitoring device 60 shown in FIG. 1 or in sense heads 200, 300, 400, 500, 600 described below; with the remaining components of external control module 126 being provided in control box 64 and/or between control box 64 and monitoring device 60 or sense heads 200, 300, 400, 500, 600 described below. A TET drive circuit 134 controls the application of a power signal to primary TET coil 130. TET drive circuit 134 is controlled by a microprocessor 136 having an associated memory 138. A graphical user interface 140 is connected to microprocessor 136 for controlling the data shown on a display associated with the system, including but not limited to display 66.

External control module 126 also includes a primary telemetry transceiver 142 for transmitting interrogation commands to and receiving response data, including fluid pressure readings, from implant control module 132. Primary transceiver 142 is electrically connected to microprocessor 136 for inputting and receiving command and data signals. Primary transceiver 142 resonates at a selected RF communication frequency to generate a downlink alternating magnetic field 146 that transmits command data to implant control module 132. A power supply 150 supplies energy to external control module 126 in order to power system 30. An ambient pressure sensor 152 is connected to microprocessor 136. Microprocessor 136 uses the signal from ambient pressure sensor 152 to adjust the pressure reading for variations in atmospheric pressure due to, for example, variations in barometric conditions or altitude, in order to increase the accuracy of the pressure measurement. Of course, external control module 126 may include a variety of other components, features, and/or functionalities, in addition to or in lieu of those explicitly described herein, as will be apparent to those of ordinary skill in the art in view of the teachings herein.

FIG. 7 also illustrates exemplary internal control module 132 implanted beneath the patient's skin 154. Internal control module 132 may be located at least partially within injection port 42, although this is not required. As shown in FIG. 7, a secondary TET/telemetry coil 156 in internal control module 132 receives power and communication signals from external control module 126. Coil 156 forms a tuned tank circuit that is inductively coupled with either primary TET coil 130 to power the implant and/or primary telemetry coil 144 to receive and transmit data. A telemetry transceiver 158 controls data exchange with coil 156. Additionally, internal control module 132 includes a rectifier/power regulator 160, microcontroller 106 described above, a memory 162 associated with the microcontroller 106, temperature sensor 112, pressure sensor 84, and a signal conditioning circuit 164 for amplifying the signal from the pressure sensor. Internal control module 132 transmits the temperature adjusted pressure measurement from pressure sensor 84 to external control module 126. In external module 126, the received pressure measurement signal is adjusted for changes in ambient pressure and may be shown on an associated display 66. Of course, internal control module 132 may include a variety of other components, features, and/or functionalities, in addition to or in lieu of those explicitly described herein, as will be apparent to those of ordinary skill in the art in view of the teachings herein.

It should also be understood that external control module 126 and/or internal control module 132, including portions thereof, may be configured and/or operable in accordance with the teachings of U.S. Pub. No. 2006/0211914, entitled "System and Method for Determining Implanted Device Positioning and Obtaining Pressure Data" published Sep. 21, 2006 (now U.S. Pat. No. 7,775,215), the disclosure of which is incorporated by reference herein.

Figure 8:
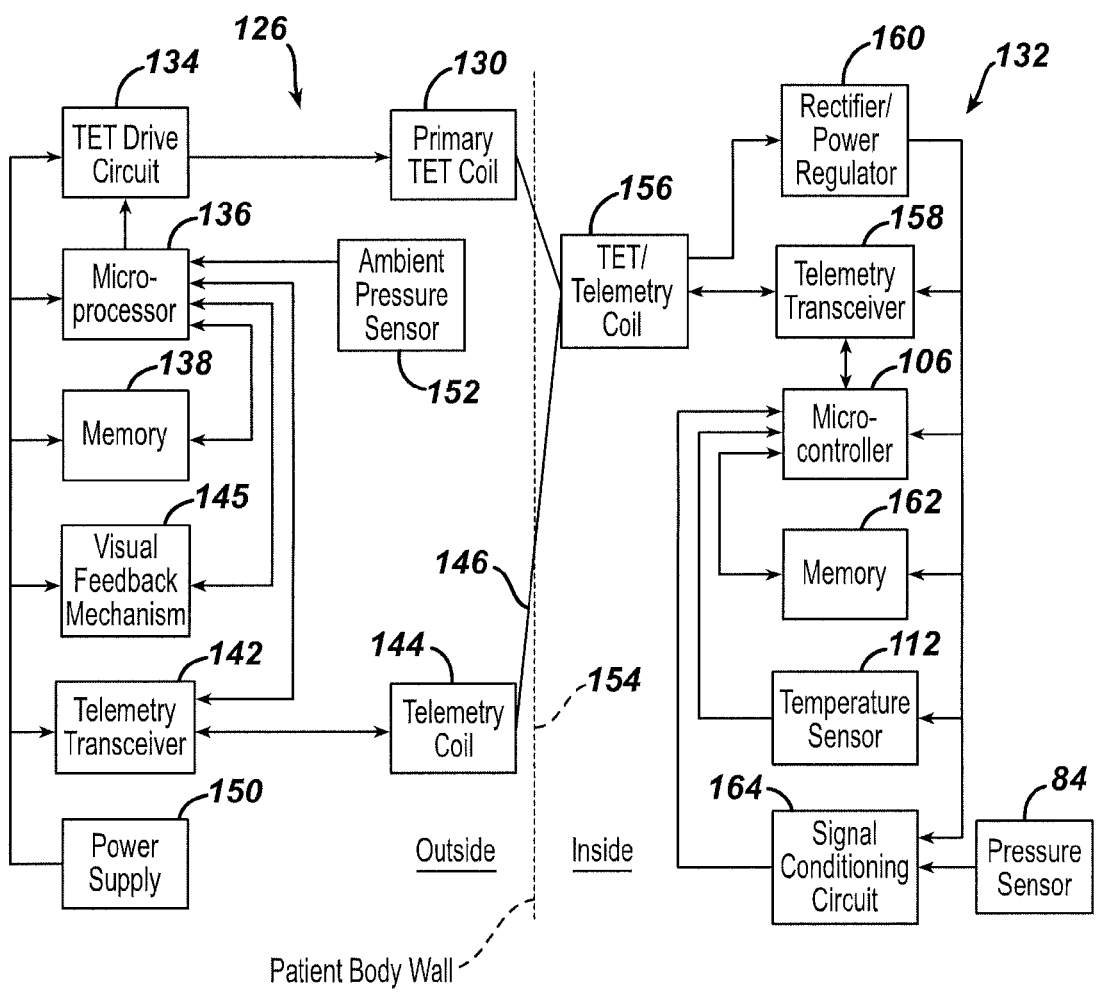
FIG. 8 depicts a block diagram representing an exemplary alternative pressure measurement and location identification system.

FIG. 8 depicts a block diagram of an alternate embodiment of a pressure measurement and location identification system. The components of the system shown in FIG. 8 are substantially similar to the system shown in FIG. 7. However, in the system shown in FIG. 8, a visual feedback mechanism 145 is incorporated within external control module 126 and configured to provide visual feedback to a user based on data communicated from internal control module 132 to external control module 126. The data may comprise pressure data, location data, orientation data, signal strength, or any other suitable data communicated between the internal control module 132 and the external control module 126. Visual feedback mechanism 145 may comprise a graphical user interface, such as graphical user interface 140 described above, configured to allow a user to control the data shown on a display associated with the system, such as display 66, although this is not required. Alternatively, visual feedback mechanism 145 may include a visual indicator incorporated within monitoring device 60 or sense heads 200, 300, 400, 500, 600, and visual feedback mechanism 145 may be configured to control data shown on such a visual indicator. In some such versions, visual feedback mechanism 145 may be configured to receive input from a user to affect the data displayed or the manner in which the data is displayed, although this is not required. The visual indicator 145 may comprise a single LED, a plurality of LEDs arranged in any suitable configuration, an LCD display, or any other suitable indicator or display configured to provide a visual indication of data to the user.

Figure 9:
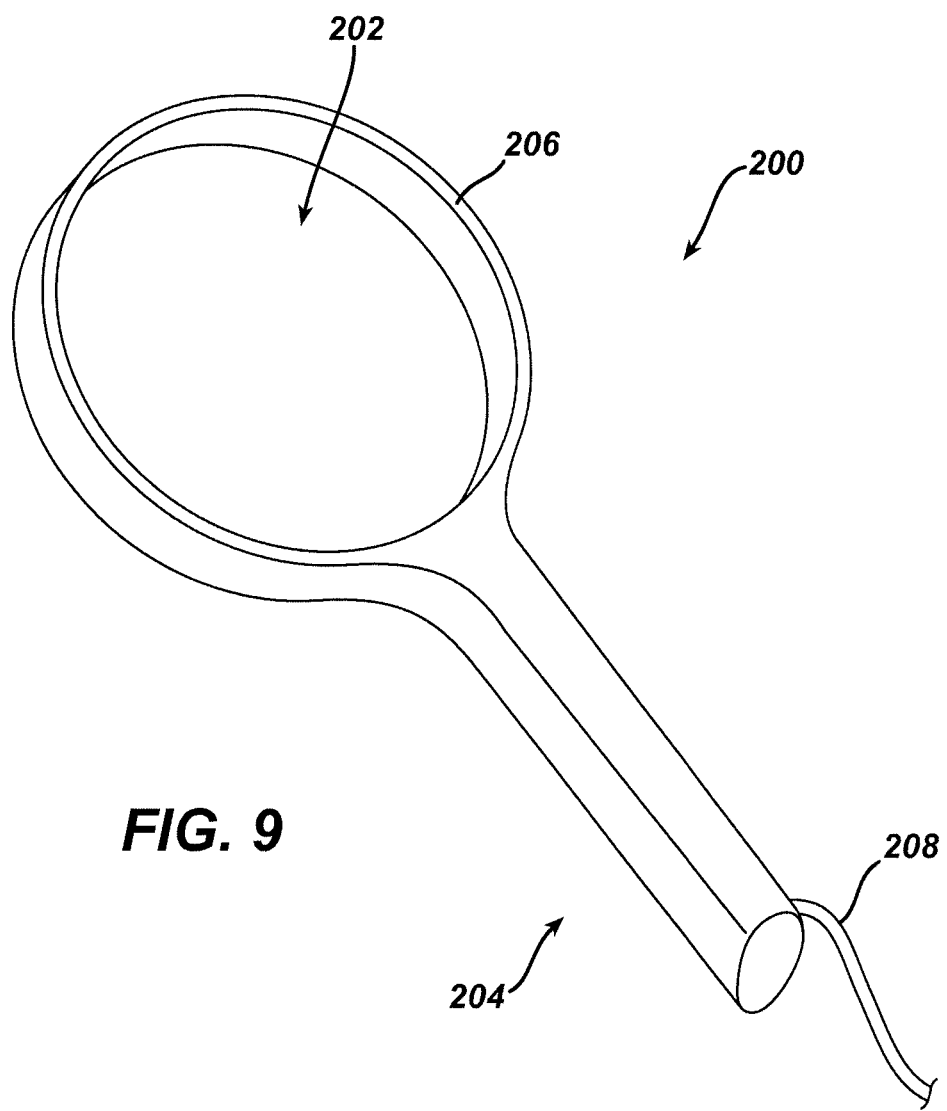
FIG. 9 depicts a perspective view of an exemplary sense head.

FIG. 9 depicts an exemplary version of a sense head 200, which is one type of external monitoring device. Sense head 200 may incorporate at least a portion of external control module 126 and be configured to locate an implanted device, such as port 42, incorporating internal control module 132. In particular, sense head 200 may include coils 130, 144. By way of example only, a user may pass sense head 200 over a patient in search of port 42. As sense head 200 approaches port 42 the strength of the signal communicated between sense head 200/external control module 126 and port 42/internal control module 132 may increase. When the signal strength reaches a predefined intensity level, or when the signal strength is at its maximum, then that may serve as an indicator that sense head 200 is substantially aligned with port 42. Sense head 200 may provide a visual indication of signal strength on an external display device or a display device integrated within sense head 200 or on sense head handle 204. The visual indication may be provided via a single LED, a plurality of LEDs arranged in any suitable configuration, an LCD display, or any other suitable indicator or display configured to provide a visual indication of signal strength to the user. Alternatively, sense head 200 may provide an auditory signal or other suitable indication of signal strength. Sense head 200 may otherwise provide an indication of signal strength or port 42 location in accordance with the teachings of U.S. Pub. No. 2006/0211914, entitled "System and Method for Determining Implanted Device Positioning and Obtaining Pressure Data" published Sep. 21, 2006 (now U.S. Pat. No. 7,775,215), the disclosure of which is incorporated by reference herein.

The signal strength may be maximized when the center of telemetry coil 144 in sense head 200 is substantially aligned with the center of secondary TET/telemetry coil 156 in internal control module 132. Sense head 200 may be configured such that the center of telemetry coil 144 is aligned with the center of opening 202 of sense head 200, and port 42 may be configured such that the center of secondary TET/telemetry coil 156 is aligned with the center of port 42, although this configuration is not necessarily required. In some such versions, the signal strength may be maximized when the center of opening 202 of sense head 200 is substantially aligned with the center of port 42. Accordingly, in this example, a needle inserted into the patient at the center of opening 202 will successfully reach septum 76 of port 42. In some other versions, TET/telemetry coil 156 may be positioned such that the center of TET/telemetry coil 156 is not aligned with the center of port 42. In some such versions, a user may be able to locate port 42 by detecting the center of TET/telemetry coil 156 with sense head 200 via signal strength and offsetting the distance between the center of TET/telemetry coil 156 and the center of port 42. In this example, a user may insert a needle at the offset point in order to successfully reach septum 76 of port 42.

As shown in FIG. 9, sense head 200 comprises a handle portion 204 configured to allow a user to grasp sense head 200 and pass sense head 200 over the patient in order to locate an implanted device and/or receive other data from an implanted device. Sense head 200 may be constructed as either a disposable or a reusable component. Handle portion 204 may be may be ergonomically molded to correspond to the shape of a user's fingers and/or it may comprise one or more features such as recesses, ridges, knurling, or any other feature suitable to facilitate grasping by a user. Of course, such features are not required and may be omitted entirely. In the illustrated example, sense head 200 further comprises a head portion 206. As shown, head portion 206 comprises an annular member. However, head portion 206 may comprise any suitable shape, including, but not limited to annular, rectangular, square, and triangular. Similarly, opening 202 is circular in the illustrated embodiment. But, opening 202 may comprise any suitable shape, including, but not limited to circular, ovular, elliptical, rectangular, square, or triangular. Coils 130, 144 are provided in head portion 206 in this example, such that coils 130, 144 encircle opening 202. Again, though, coils 130, 144 may be consolidated into a single coil, if desired. Various ways in which TET and telemetry functions may be provided by a single coil will be apparent to those of ordinary skill in the art in view of the teachings herein.

As shown in FIG. 9, sense head 200 of the present example further comprises electrical cable assembly 208, which may connect sense head 200 to any suitable external device, including but not limited to control box 64, and/or a power source. Electrical cable assembly 208 is in communication with coils 130, 144 in sense head 200. Electrical cable assembly 208 is shown as being attached to handle portion 204. However, it may be attached to head portion 206 or any other suitable location in other versions. In some versions, electrical cable assembly 208 may be omitted entirely and sense head 200 may wirelessly communicate with external devices and/or receive power from an internal power source integrated within sense head 200. The components of sense head 200, including head portion 206 and handle portion 204 may be integral or separable with each other. In versions wherein the components are separable, one or more of the components may be constructed as reusable or disposable components. Still other suitable components, features, configurations, and functionalities of a sense head 200 will be apparent to those of ordinary skill in the art in view of the teachings herein.

Figure 10:
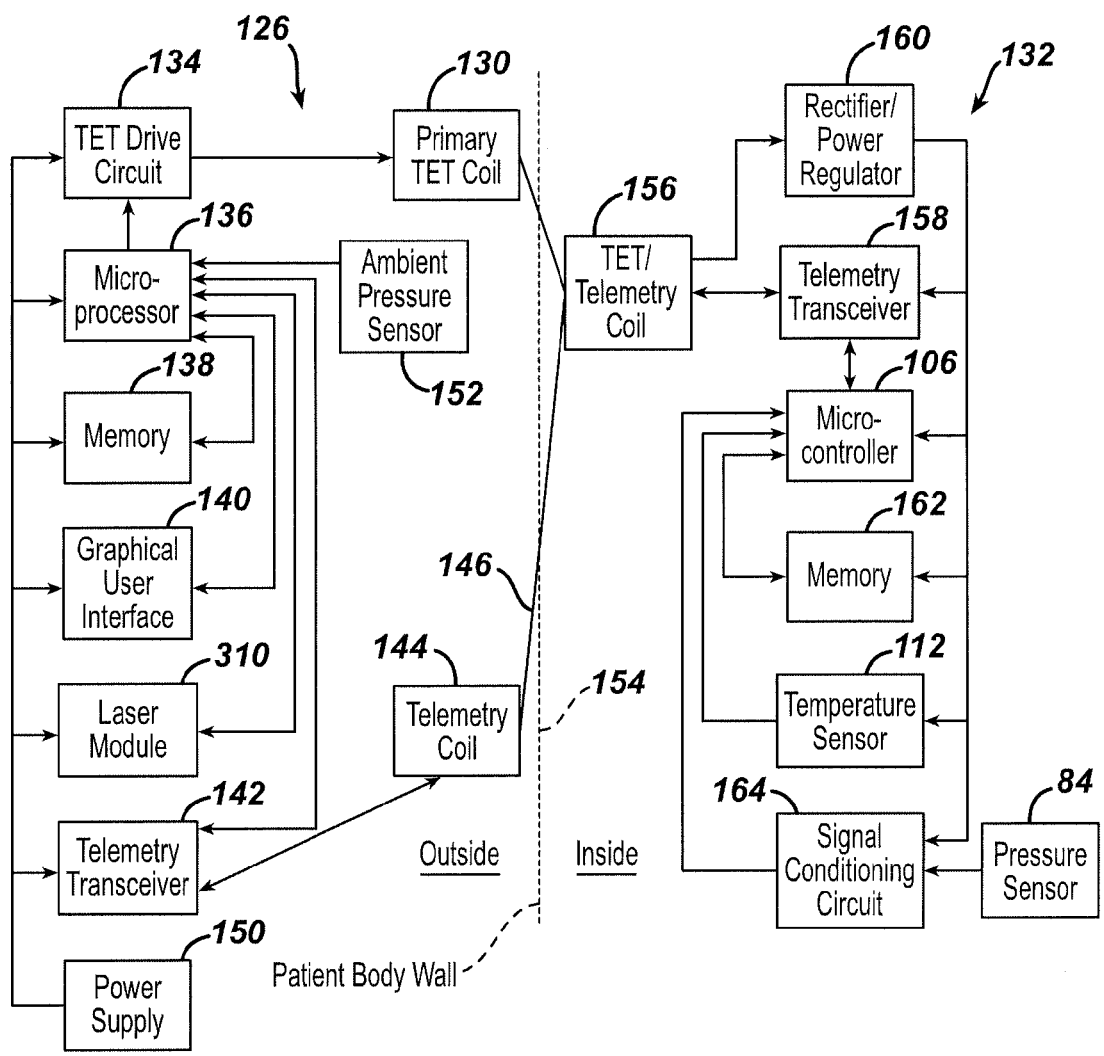
FIG. 10 depicts a block diagram representing another exemplary alternative pressure measurement and location identification system.

FIG. 10 depicts a block diagram of another exemplary pressure measurement and location identification system. The components of the system shown in FIG. 10 are substantially similar to the system shown in FIG. 7. However, in the system shown in FIG. 10, a laser module 310 is incorporated within external control module 126 and is configured to provide visual feedback to a user. The visual feedback may include but is not limited to the intersection of two or more lasers or a single laser pointing to a specific point/location. In some versions, laser module 310 may be configured to provide a visual indication of the center of opening 202. In some versions, laser module 310 may be configured to provide a visual indication of the location of an implanted device, such as port 42, based on data communicated from internal control module 132 to external control module 126. In some versions, such as those described above, the center of opening 202 will approximately coincide with the location of the implanted port 42, and hence, the septum 76 of port 42. Accordingly, laser module 310 may be configured to provide a visual indication of both the center of opening 202 and the approximate location of septum 76 of an implanted port 42.

Laser module 310 may be configured to control one or more lasers incorporated within a sense head, such as sense head 300 shown in FIG. 11 and described below. Laser module 310 may be configured to selectively power the one or more lasers in response to the strength of the signal between internal control module 132 and external control module 126 reaching a pre-determined level. For instance, a signal strength threshold may be stored in memory 138. Microprocessor 136 may be configured to compare signal strength from coil 144 against this threshold stored in memory 138, and activate laser module 310 when the signal strength exceeds the threshold. Alternately, laser module 310 may be configured to continuously power the one or more lasers irrespective of signal strength between internal control module 132 and external control module 126; or to allow a user to selectively power the one or more lasers irrespective of the signal strength between internal control module 132 and external control module 126.

Additionally, laser module 310 may be configured to control and/or adjust one or more characteristics of the beam(s) produced by the one or more lasers. By way of example only, laser module 310 may vary one or more of the following characteristics of the beam(s) including but not limited to the color of the beam(s), the brightness of the beam(s), and the integrity of the beam(s) (i.e. whether the beam is solid or pulsating/flickering). Laser module 310 may vary one or more characteristics according to the strength of the signal between internal control module 132 and external control module 126 or any other suitable factor(s), although this is not required. For example, in some versions the beam(s) may pulsate at a specified rate until signal strength reaches a pre-determined level, at which point the beam(s) may become solid and cease pulsating. In some other versions, the beam(s) may comprise a first color, such as red until signal strength reaches a pre-determined level, at which point the beam(s) may transition to a second color, such as green. Of course other suitable colors and any suitable number of different colors, including three or more, may be used. In still other versions, the beam(s) may have a first brightness level until signal strength reaches a pre-determined level, at which point the beam(s) may have a second brightness level that is greater than the first brightness level. Alternately, the brightness level may be increased and decreased gradually in accordance with variations in the signal strength between internal control module 132 and external control module 126. Various other ways in which laser characteristics may be varied, based on signal strength and/or other conditions, will be apparent to those of ordinary skill in the art in view of the teachings herein.

Figure 11:
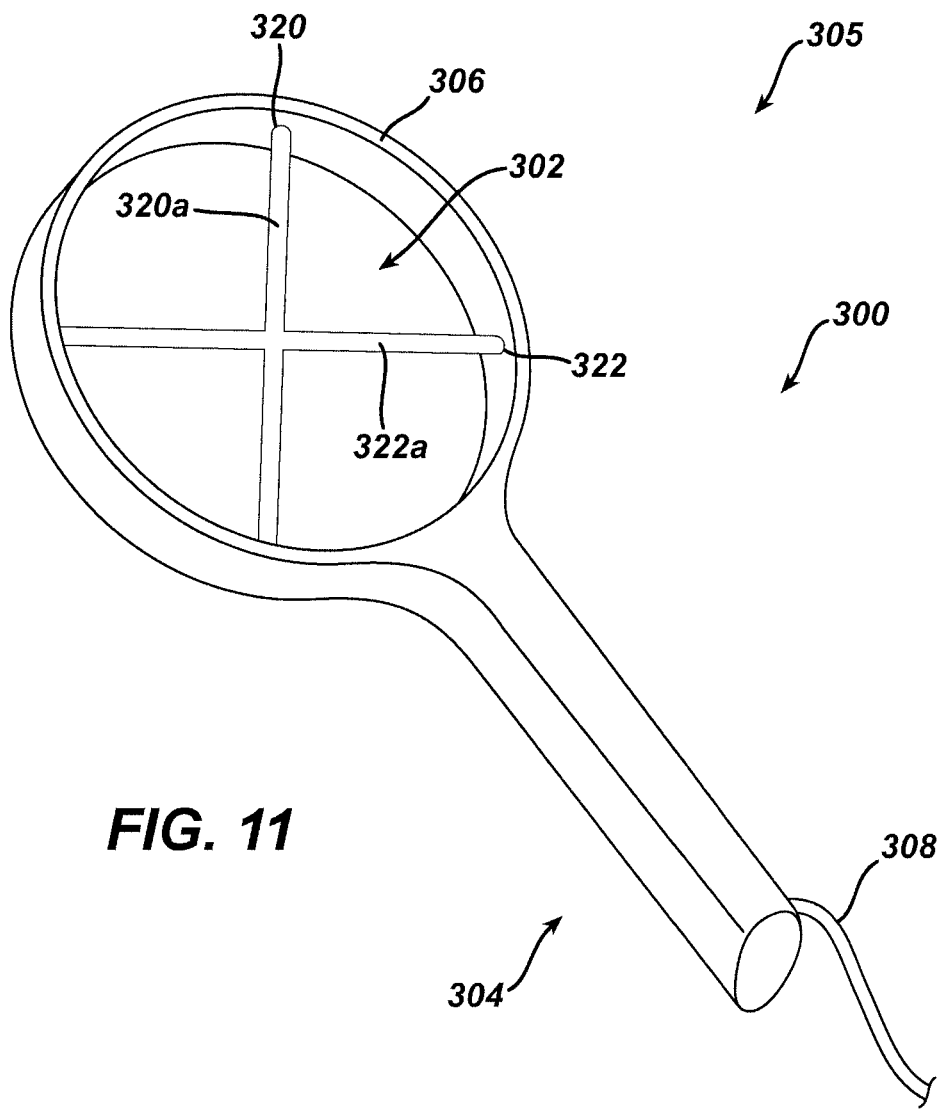
FIG. 11 depicts a perspective view of an exemplary needle targeting apparatus incorporating the sense head of FIG. 8 and a laser guide.

FIG. 11 depicts an exemplary needle targeting apparatus 305 comprising a sense head 300 that incorporates a pair of lasers 320, 322. Of course, any suitable number of lasers may be used, including one, two, three or more. Sense head 300 may include at least a portion of external control module 126 that incorporates laser module 310, as well as coils 130, 144 and/or any other suitable components. Sense head 300 is similar to sense head 200 depicted in FIG. 9 and described above, other than the addition of lasers 320, 322. Accordingly, sense head 300 comprises an opening 302, a handle portion 304, a head portion 306, and an electrical cable assembly 308. Each of the components is similar to the corresponding component described above with regard to sense head 200. As shown in FIG. 11, lasers 320, 322 are incorporated within head portion 306 and are arranged so that the beams 320a, 322a produced by lasers 320, 322 intersect. The intersection of beams 320a, 322a may indicate the center of opening 302, the location of the approximate center (e.g., septum 76) of an implanted device (e.g., port 42), or both the center of opening 302 and the location of approximate center of an implanted device.

In some versions where the intersection of beams 320a, 322a indicates the approximate location of port 42 (or even the approximate location of septum 76), the user may utilize sense head 300 to indicate a proper insertion point for inserting a needle into septum 76 port 42. In such versions, once port 42 is located, the user may identify the proper insertion point by marking the patient at the intersection of beams 320a, 322a with a marker or other writing instrument. The user may remove sense head 300 and successfully insert the syringe into septum 76 of port 42 by inserting the syringe into the patient at the insertion point indicated by the marking. Alternatively, the user may hold or leave sense head 300 in place once port 42 is located and successfully insert the syringe into septum 76 of port 42 by inserting the syringe into the patient through opening 302 at the intersection of beams 320a, 322a. Various other suitable ways in which sense head 300 may be configured and used will be apparent to those of ordinary skill in the art in view of the teachings herein.

Figure 12:
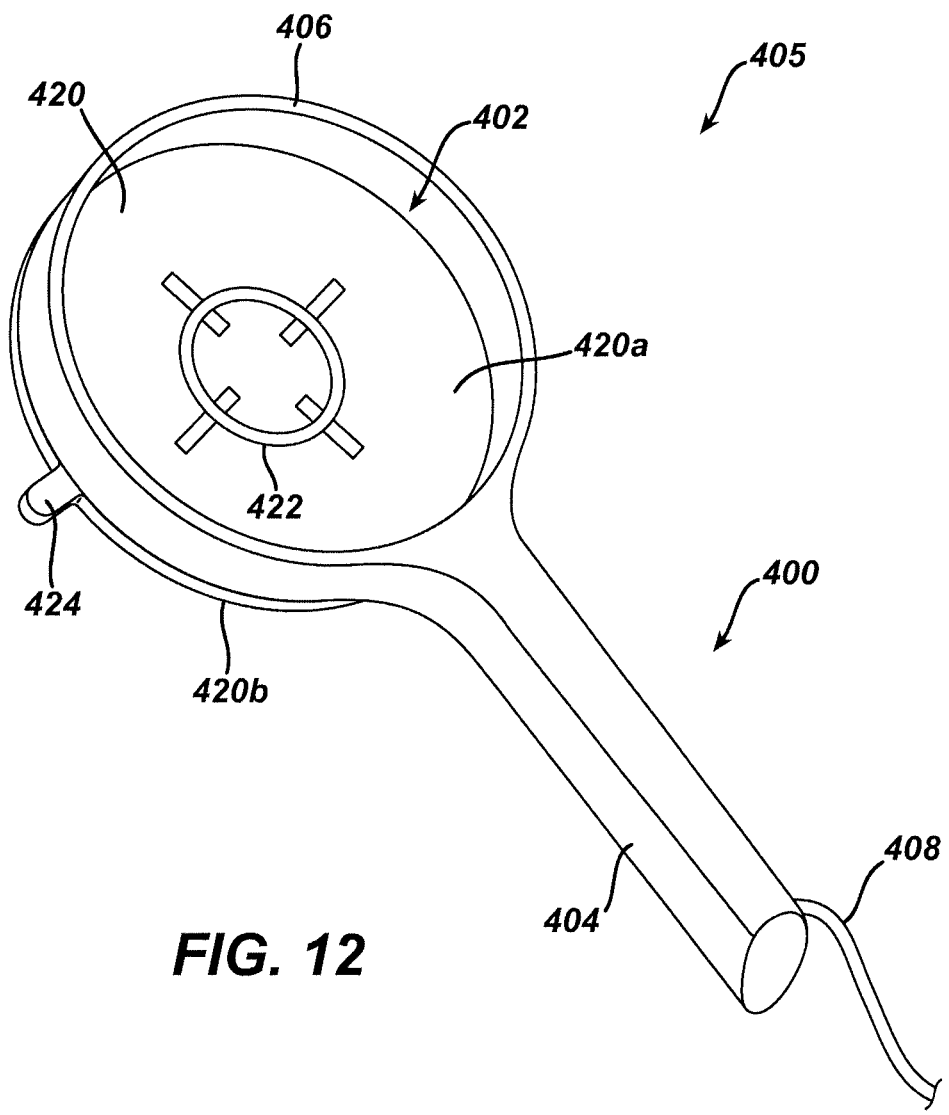
FIG. 12 depicts a perspective view of an exemplary alternative needle targeting apparatus incorporating the sense head of FIG. 8 and a piece of sheet material.
Figure 13:
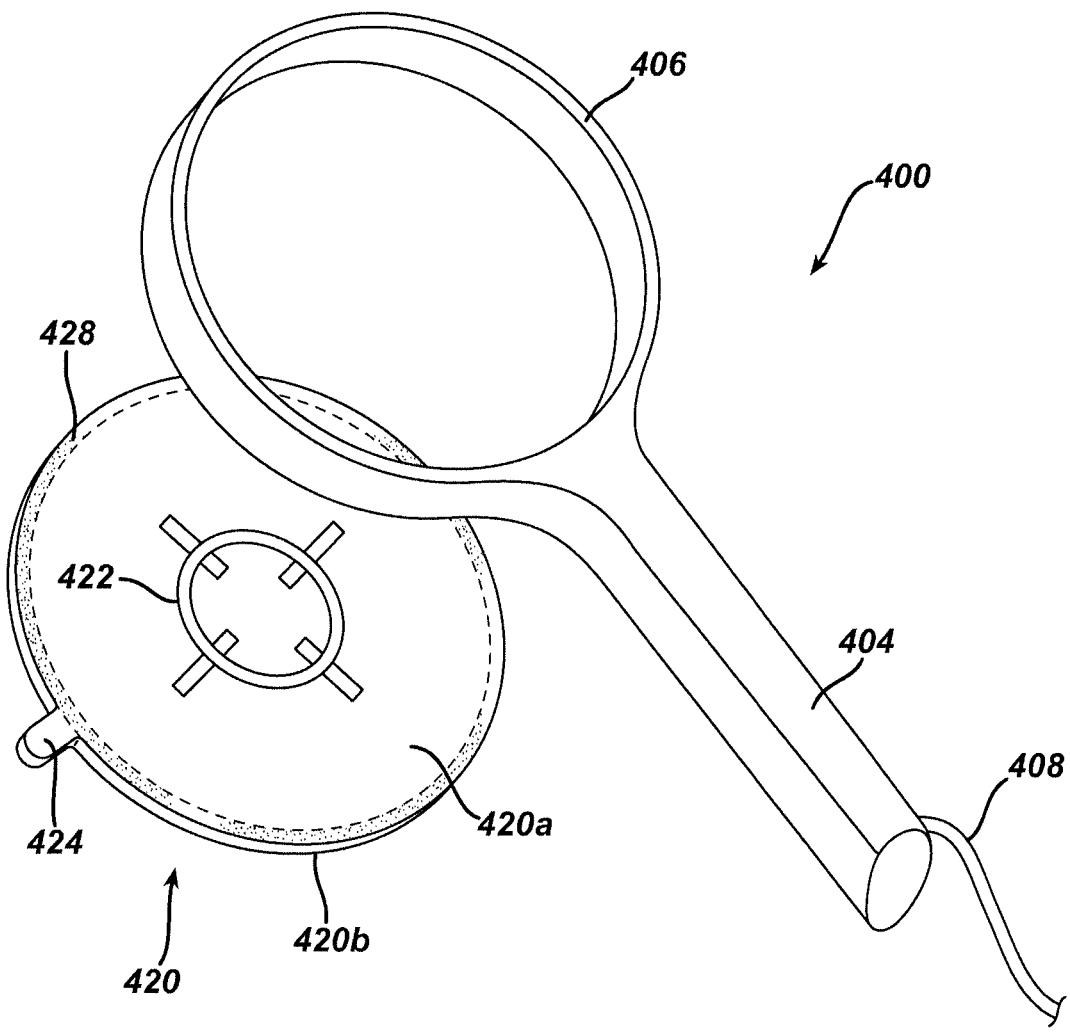
FIG. 13 depicts a perspective assembly view of the needle targeting apparatus of FIG. 12.

FIGS. 12-13 depict another exemplary needle targeting apparatus 405 comprising a sense head 400 and a needle guide 420. Sense head 400 is similar to sense head 200 depicted in FIG. 9 and described above. Accordingly, sense head 400 comprises an opening 402, a handle portion 404, a head portion 406, and an electrical cable assembly 408. Sense head 400 also includes coils 130, 144 encircling opening 402. Each of the components is similar to the corresponding components described above with regard to sense head 200. Sense head 400 may include at least a portion of an external control module, such as portions of external control module 126 depicted in FIGS. 7 and 8. As a result, sense head 400 may be configured to locate an implanted device, such as port 42.

In the present example, needle guide 420 comprises an upper surface 420a, a lower surface 420b, a target 422 and a pull tab 424. Guide 420 may comprise any suitable material, including but not limited to a piece of transparent, disposable plastic film. As shown, guide 420 is sized and shaped to correspond to the shape of head portion 406 of sense head 400. This is not required, and guide 420 may be suitably sized and shaped to engage head portion 406 without necessarily having a corresponding size and shape. Guide 420 may be constructed as a disposable or a reusable component.

In this example, target 422 comprises a set of crosshairs aligned with the center of guide 420, and, correspondingly, the center of opening 402 when sense head 400 and guide 420 are engaged with each other. Of course, target 422 may comprise any suitable structure or feature configured to provide an indication to the user where to insert a syringe needle in order to successfully reach an implanted device, including but not limited to a cross, a bulls-eye, a dot, arrows, or a circle. In embodiments wherein the center of TET/Telemetry coil 156 is not aligned with the center of port 42, target 422 may further include gradients to aid the user in measuring the known offset distance between the center of TET/Telemetry coil 156 and the center of port 42 in order to allow a user to accurately locate port 42 and properly insert a syringe needle in septum 76. In addition, target 422 may be placed in any suitable location on guide 420, including but not limited to the center of guide 420 or a position offset a specific distance from the center of guide 420. In some versions, an interior portion of target 422 may be hollow or have an opening formed therethrough so that a user may insert a syringe through opening 402 and into an implanted device without having to pierce guide 420.

Pull tab 424 may be configured to allow a user to manipulate guide 420 during use of needle targeting apparatus 405. Pull tab 424 may be positioned in any suitable location on guide 420, including but not limited to along an edge of guide 420 as shown in FIGS. 12 and 13. Of course, more than one pull tab 424 may be provided, and pull tab(s) 424 may have any other suitable configuration. Alternatively, pull tab 424 may be modified, substituted, supplemented, or omitted as desired.

In the present example, guide 420 is releasably engaged with head portion 406 of sense head 400. In some other versions, guide 420 may be fixedly engaged with sense head 400. Strip 428 may extend around substantially the entire perimeter of guide 420, as shown in FIG. 13, or, alternatively, strip 428 may only extend around a portion of the perimeter of guide 420. In some versions, strip 428 comprises double sided adhesive (e.g., a pressure-sensitive adhesive). For instance, a strip 428 may comprise an adhesive applied to both upper surface 420*a* and lower surface 420*b* of guide 420. Accordingly, adhesive on upper surface 420*a* may removably adhere guide 420 to head portion 406 of sense head 400; while adhesive on lower surface 420*b* of guide 420 may removably adhere guide 420 to a patient's skin or other surfaces, such as a sterile drape. In some such versions, the adhesive positioned to engage the patient's skin may create a stronger bond between guide 420 and the patient's skin than the bond created between guide 420 and head portion 406, although this is not required. In some versions, an adhesive is only applied along circumferential strip 428 on upper surface 420*a*; while an adhesive is applied along the entire lower surface 402*b* (or at least along a portion of lower surface 420*b* occupying more surface area than the surface area of upper surface 420*a* along which adhesive is applied).

In some other versions, strip 428 may comprise single sided adhesive, wherein the adhesive is only on the upper surface 420*a* of guide 420 to engage head portion 406. In such versions, the user may peel sense head 400 away from guide 420 after port 42 has been suitably located, and manually hold guide 420 in place against the patient's skin until a needle has been successfully inserted through target 422. In still other versions, strip 428 may comprise single sided adhesive, wherein the adhesive is only on the lower surface 420*b* of guide 420 to engage a patient's skin or other surface. In such versions, guide 420 may be engaged with sense head 400 in any suitable manner including but not limited to a tab inserted into an opening in head portion 406, one or more clips or suction cups on head portion 406 configured to grasp guide 420, a raised lip extending along a portion of guide 520 and corresponding opening in head portion 406, a vacuum between head portion 406 and guide 420, hook and pile fasteners, plastic snap features, buttons, a screw mechanism, etc.

Strip 428 may further comprise an alcohol agent or some other type of agent to disinfect the area and allow for the needle to pass through a sterile environment.

In versions where guide 420 incorporates adhesive, guide 420 may further comprise a removable protective strip (not shown) configured to cover at least a portion of the adhesive. Guide 420 may comprise a first protective strip covering at least a portion of the adhesive on the upper surface 420*a* of guide 420 (e.g., the adhesive configured to engage head portion 406) and a second protective strip covering at least a portion of the adhesive on the lower surface 420*b* of guide 420 (e.g., the adhesive configured to engage a patient's skin) The first protective strip and the second protective strip may be removable. To expose the adhesive, to allow the adhesive.

In one exemplary method of using needle targeting apparatus 405, a user may begin by engaging needle guide 420 and sense head 400. A releasable engagement may be accomplished by removing the first protective strip covering adhesive on the upper surface 420*a* of guide 420, thereby exposing the adhesive, and pressing the upper surface 420*a* of guide 420 against sense head 400 such that at least a portion of head portion 406 contacts the adhesive. As mentioned above other suitable configurations and methods of engaging needle guide 420 and sense head 400 will be apparent to those skilled in the art. Once needle guide 420 and sense head 400 are engaged, then the user may pass sense head 400 over patient to locate an implanted device, such as port 42, by monitoring signal strength as described herein or using any other suitable techniques. After locating port 42, the user may remove the second protective strip covering adhesive on the lower surface 420*b* of guide 420. With the adhesive exposed, the user may releasably secure needle guide 420 adjacent to the injection site by pressing guide 420 against the patient's skin. Sense head 400 may be separated from needle guide 420, although this is not required. Finally, the user may utilize target 422 to identify the proper injection site and successfully insert a syringe needle into septum 76 of port 42. Various other suitable ways in which targeting apparatus 405 may be configured and used will be apparent to those of ordinary skill in the art in view of the teachings herein.

Figure 14:
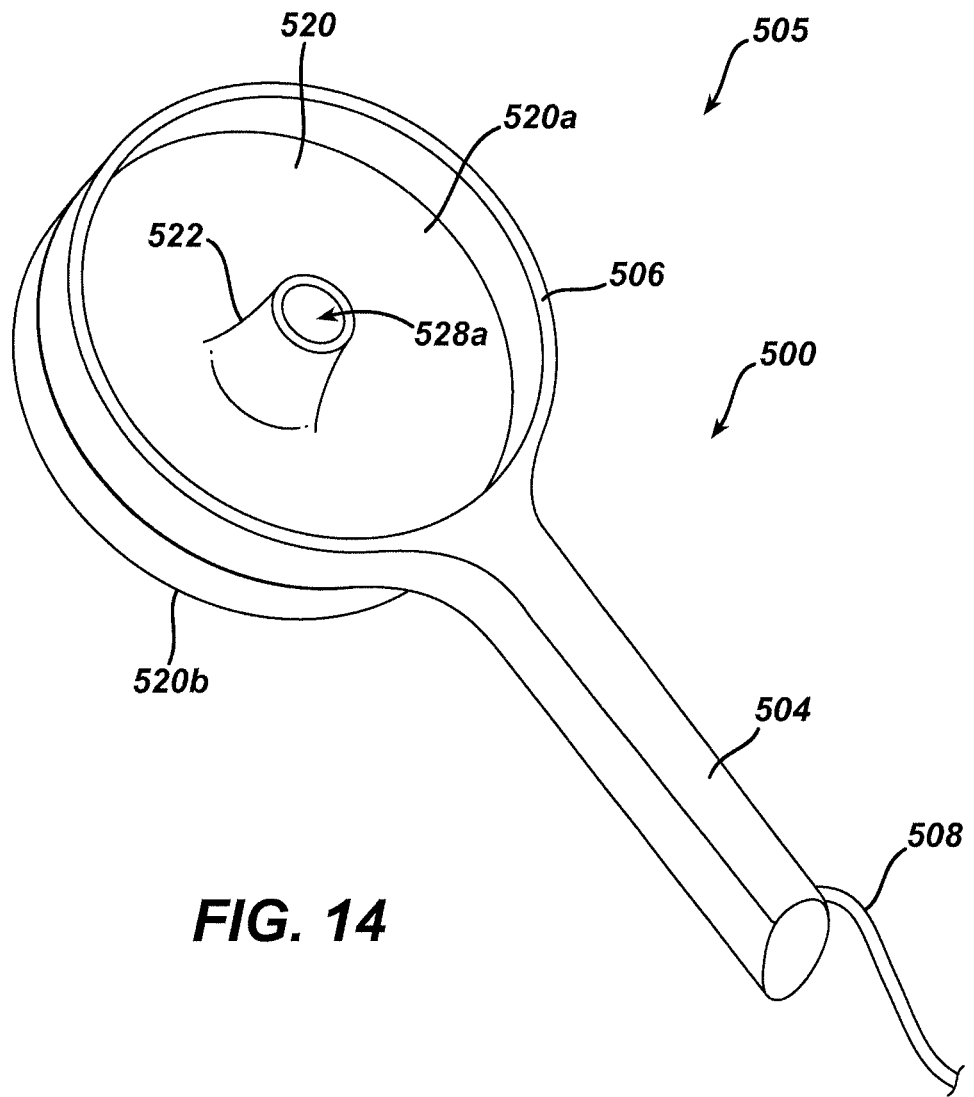
FIG. 14 depicts a perspective view of an exemplary alternative needle targeting apparatus incorporating the sense head of FIG. 8 and an insert.
Figure 15:
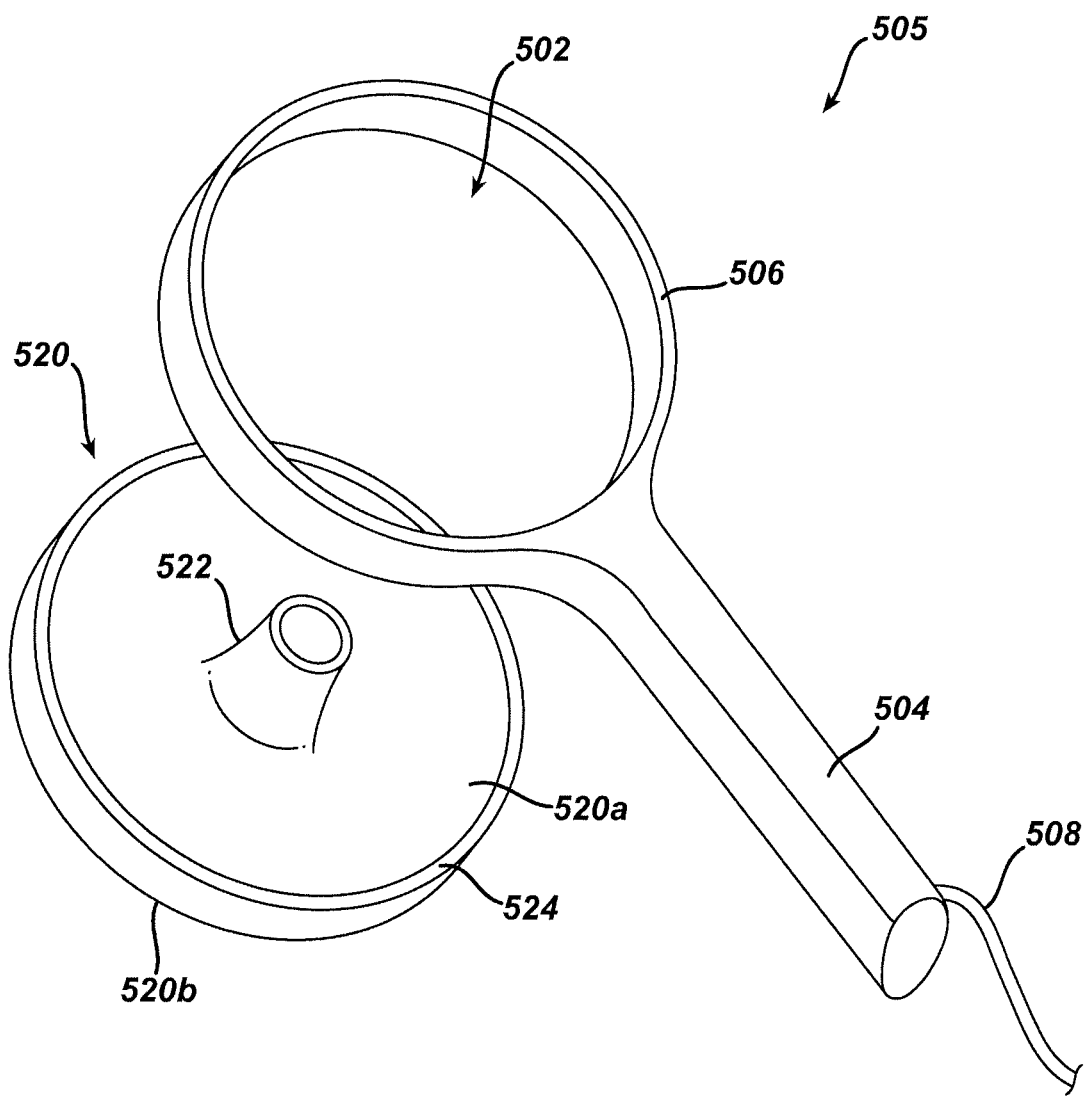
FIG. 15 depicts a perspective assembly view of the needle targeting apparatus of FIG. 14.
Figure 16:
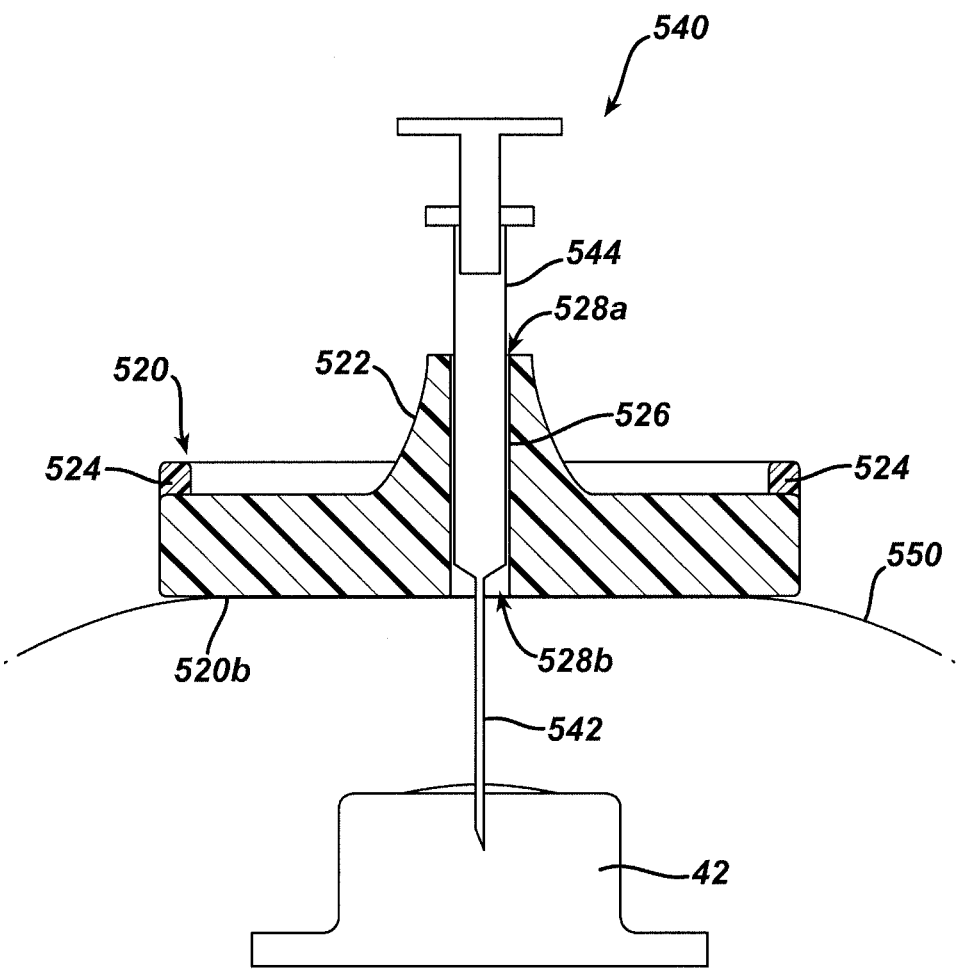
FIG. 16 depicts a side, cross-sectional view of a component of the needle targeting apparatus of FIG. 14 and a syringe inserted into an implanted device.

FIGS. 14-16 depict another exemplary needle targeting apparatus 505 comprising a sense head 500 and a needle guide 520. Sense head 500 is similar to sense head 200 depicted in FIG. 9 and described above. Accordingly, sense head 500 comprises an opening 502, a handle portion 504, a head portion 506, and an electrical cable assembly 508. Sense head 500 also includes coils 130, 144 encircling opening 502. Each of the components is similar to the corresponding component described above with regard to sense head 200. Sense head 500 may include at least a portion of an external control module, such as external control module 126 depicted in FIGS. 7 and 8. As a result, sense head 500 may be configured to locate an implanted device, such as port 42.

In the present example, needle guide 520 comprises an upper surface 520*a*, a lower surface 520*b*, a support member 522, and an engagement feature 524. As shown, guide 520 is sized and shaped to correspond to the shape of head portion 506 of sense head 500. This is not required, and guide 520 may be suitably sized and shaped to engage head portion 506 without necessarily having a corresponding size and shape.

Guide 520 may be constructed as a disposable or a reusable component. As shown, support member 522 is positioned at the center of guide 520 and, correspondingly, the center of opening 502 when sense head 500 and guide 520 are engaged with each other. In alternate embodiments, support member 522 may be placed in any suitable location on guide 520, including but not limited to the center of guide 520 or a position offset a specific distance from the center of guide 520.

As shown in FIGS. 14-16, support member 522 comprises a raised portion that extends in a substantially vertical direction from upper surface 520a. Support member 522 further comprises a channel 526 that extends through support member 522 between an upper opening 528a at the top of support member and a lower opening 528b in lower surface 520b. Channel 526 may be configured to receive at least a portion of a syringe 540. As shown in FIG. 16, channel 526 is configured to allow a syringe needle 542 to reach an injection site while simultaneously receiving and supporting at least a portion of a syringe barrel 544. The interior walls of channel 526 may be substantially smooth, or, alternatively, the interior walls of channel 526 may comprise one or more gripping features, including but not limited to ribs, configured to facilitate the engagement between syringe barrel 544 and support member 522. Support member 522 may comprise any suitable material, including but not limited to elastomeric or malleable material configured to facilitate engagement between support member 522 and syringe 540 and to allow support member 522 to receive and support different sizes of syringes. In some versions (not shown), channel 526 may comprise an hourglass shape configured to permit a syringe needle to be inserted at an oblique angle relative to the patient's skin. As shown, support member 520 is positioned at the center of guide 520. Of course, other suitable positions for support member 520 will be apparent to those skilled in the art. In particular, in embodiments wherein the center of TET/Telemetry coil 156 is not aligned with the center of port 42, support member 522, and more specifically lower opening 528a, may be located off-center in order to accurately locate septum 76 of port 42 and allow a user to properly insert a syringe needle therein.

In the present example, engagement feature 524 comprises a raised lip that extends along the perimeter of guide 520. In this example, head portion 506 comprises a corresponding opening in its bottom surface configured to releasably receive engagement feature 524. Engagement feature 524 may be sized and shaped to provide a friction fit with head portion 506, although this is not required. Alternate versions (not shown), may incorporate a locking mechanism and a release trigger to secure and release guide 520 and sense head 500 to and from each other. Of course, those skilled in the art will appreciate that engagement feature 524 is not limited to a raised lip extending along the entire perimeter of guide 520. By way of example only, engagement feature 524 may comprise a strip of adhesive on upper surface 520a, a tab inserted into an opening in head portion 506, one or more clips or suction cups on head portion 506 configured to grasp guide 520, a raised lip extending along a portion of guide 520 and a corresponding opening in head portion 506, and a vacuum between head portion 506 and guide 520. In addition, engagement feature 524 may be positioned along the perimeter of guide 520 as shown in FIGS. 14-15 or any other suitable location on guide 520. In some other versions (not shown), an engagement feature may be provided by the outer side perimeter of guide 520. In some such versions, guide 520 and head portion 506 may be sized and shaped such that the guide 520 substantially fits within opening 205 in head portion 506, resulting in a friction fit between the guide and the head portion 506. It should be understood that guide 520 and head portion 506 may be coupled in any suitable fashion, including but not limited to using hook and pile fasteners, plastic snap features, buttons, a screw mechanism, etc.

In one exemplary method of using needle targeting apparatus 505, a user may begin by engaging needle guide 520 and sense head 500. A releasable engagement may be accomplished by inserting engagement feature 524 into the opening (not shown) in head portion 506. As mentioned above other suitable configurations and methods of engaging needle guide 520 and sense head 500 will be apparent to those skilled in the art. Once needle guide 520 and sense head 500 are engaged, then the user may pass sense head 500 over patient to locate an implanted device, such as port 42. With port 42 being located, the central longitudinal axis of channel 526 may be substantially aligned with the center of septum 76 of port 42. After locating port 42, the user may disengage needle guide 520 from sense head 500 by removing engagement feature 524 from head portion 506. Lower surface 520b may comprise one or more features, such as ribs, adhesive, and/or other gripping features, to facilitate engagement between guide 520 and patient's skin 550 or other surface (e.g., sterile drape, etc.), although this is not required. As shown in FIG. 16, support member 522 is positioned within guide 520 such that support member 522, and more specifically lower opening 528b, is aligned with port 42 after sense head 500 has located port 42 and guide 520 has been disengaged from sense head 500.

As shown in FIG. 16, a user may successfully insert a syringe needle 542 into port 42 by inserting the syringe 540 into support member 522. Specifically, syringe needle 542 and a portion of syringe barrel 544 may be inserted through upper opening 528a, into channel 526, and syringe needle 542 may reach the injection site through lower opening 528b. In the present example, support member 526 is sized to receive a lower portion of syringe 540 while allowing the upper portion of syringe 540 to remain exposed so a user can freely operate syringe 540. Support member 522 is further configured to support syringe 540. In some versions, support member 522 is configured to provide sufficient support for syringe 540 to allow a user to leave syringe 540 inserted into a patient while patient is in a sitting position, without the user or patient having to hold syringe 540. Various other suitable ways in which targeting apparatus 505 may be configured and used will be apparent to those of ordinary skill in the art in view of the teachings herein.

Figure 17:
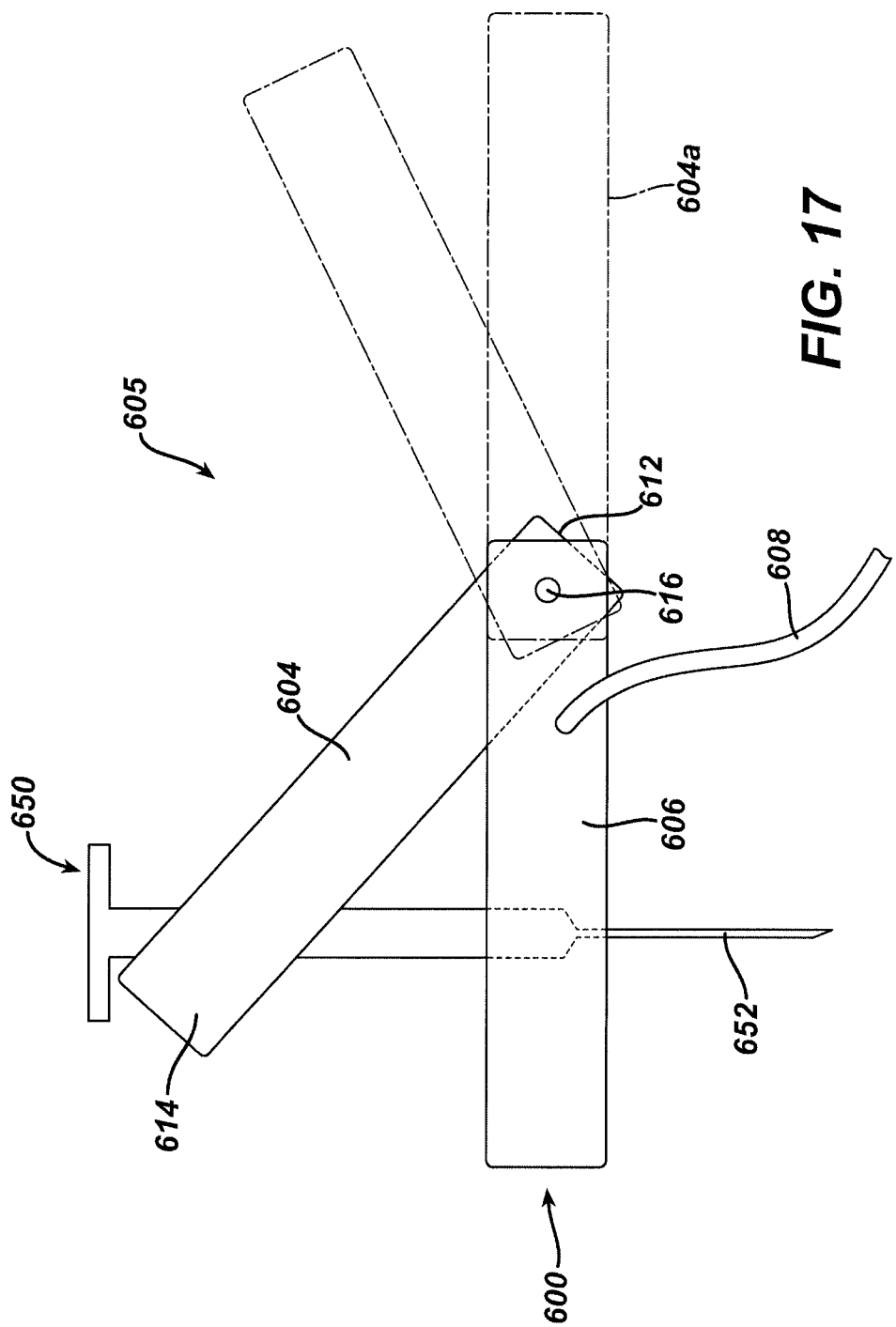
FIG. 17 depicts a side view of an alternate needle targeting apparatus incorporating an adjustable handle.
Figure 18:
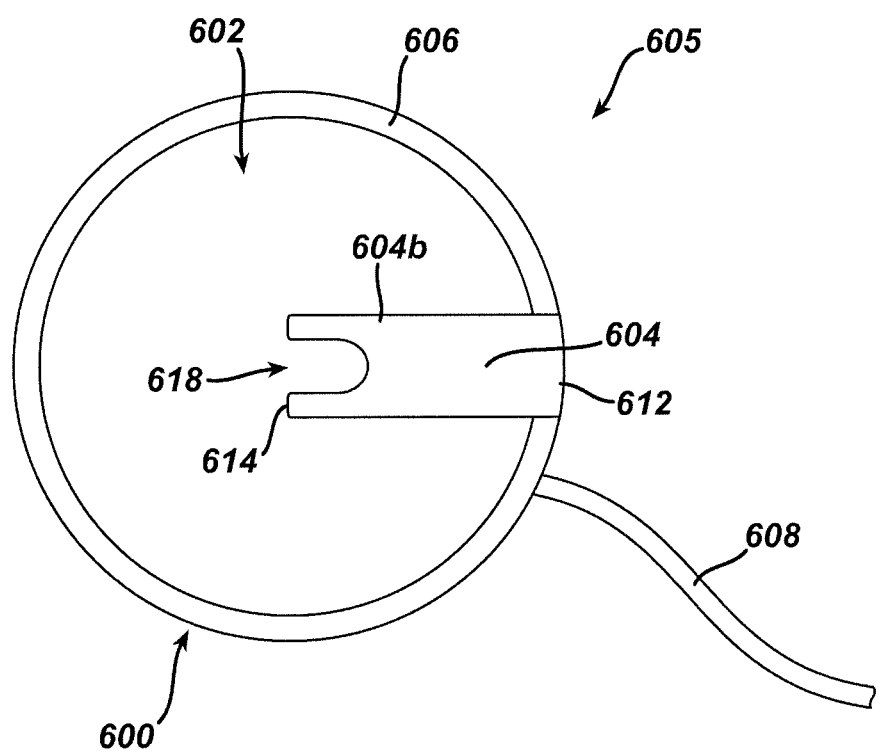
FIG. 18 depicts a top view of the needle targeting apparatus of FIG. 17.

FIGS. 17-18 depict another example of a needle targeting apparatus 605 comprising a sense head 600 having a rotatable handle portion 604. Aside from handle portion 604 being rotatable, sense head 600 is similar to sense head 200 depicted in FIG. 9 and described above. Accordingly, sense head 600 comprises an opening 602, a handle portion 604, a head portion 606, and an electrical cable assembly 608. Sense head 600 also includes coils 130, 144 encircling opening 602. Each of the components is similar to the corresponding component described above with regard to sense head 200. Sense head 600 may include at least a portion of an external control module, such as external control module 126 depicted in FIGS. 7 and 8. As a result, sense head 600 may be configured to locate an implanted device, such as port 42.

In the present example, rotatable handle 604 is configured to facilitate alignment of a needle 652 with an implanted device, such as port 42, while also providing support to a syringe 650 that is coupled with needle 652, during and after insertion of needle 652 into the implanted device. Handle portion 604 may be transitioned across a range of motion of about 180 degrees between a first position 604a and a second position 604b. Alternatively, handle portion 604 may be transitioned across a range of motion of about 360 degrees; or to any other suitable extent. As shown, in the first position 604a, handle portion 604 extends substantially horizontally outward from opening 602. In the second position 604b, handle portion 604 extends substantially horizontally inward over opening 602. Of course, handle portion 604 may be configured to engage and support a syringe 650 at any point during its rotation across the range of motion. Sense head 600 may further comprise a locking mechanism configured to selectively lock handle portion 604 into first position 604a, second position 604b, or any other position across the range of motion. For instance, such a locking mechanism may comprise one or more ratcheting features permitting handle portion 604 to be rotated from the first position 604a toward the second position 604b; while substantially preventing handle 604 from being rotated from the second position 604b back toward the first position 604a.

As shown, handle portion 604 comprises a first end 612 and a second end 614. In the present example, handle portion 604 is attached to head portion 606 at first end 612 with a hinge 616. Hinge 616 may comprise a pin, a living hinge, a ratcheting mechanism, or any other suitable connection configured to allow handle portion 604 to rotate about hinge 616. In this example, second end 614 comprises a mouth 618 configured to engage a portion of a syringe 650. In some versions, when handle portion 604 is in second position 604b, the center of mouth 618 is aligned with the center of opening 602, although this is not required. Second end 614 may comprise a gripping feature (e.g., similar to vise grips, spring-loaded clamp, etc.) that is configured to provide selective gripping and/or that is configured accommodate a plurality of syringe sizes. In addition, handle portion 604 may comprise a spring-loaded arm configured to provide selective gripping and accommodate a plurality of syringe sizes. Like support member 522 of needle guide 520 described above, handle portion 604 may provide sufficient structural support to syringe 650 when handle portion 604 is in the second position 604b to allow a user to leave syringe 650 inserted into a patient while patient is in a sitting position, without the user or patient having to hold syringe 650.

In one exemplary method of using needle targeting apparatus 605, a user may begin by grasping sense head 600 with handle portion 604 in first position 604a. As described above, the user may locate an implanted device, such as port 42, by passing sense head 600 over patient. Once the implanted device is located, the user may insert needle 652 into the implanted device by positioning syringe 650 at the center of opening 602. After inserting needle 652, then handle portion 604 may be rotated inwardly toward second position 604b until mouth 618 engages a portion of syringe 650. Alternatively, handle portion 604 may be rotated toward second position 604b after locating the implanted device but prior to insertion of syringe 650 in order to provide a further indication to user regarding the approximate location of the implanted device and a corresponding injection site. Various other suitable ways in which targeting apparatus 605 may be configured and used will be apparent to those of ordinary skill in the art in view of the teachings herein.

It should also be understood that components and features of devices described herein may be readily interchanged and combined amongst the various devices. For instance, folding handle portion 604 may be readily incorporated into needle targeting apparatus 305, needle targeting apparatus 405, or needle targeting apparatus 505. Similarly, needle targeting apparatus 605 may include lasers 320a, 322a like needle targeting apparatus 605; needle guide 420 like needle targeting apparatus 405; or needle guide 520 like targeting apparatus 505. Various other ways in which the teachings herein may be interchanged and combined among targeting apparatuses 305, 405, 505, 605 will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

It will also be readily apparent to those skilled in the art that examples described herein may have applicability to other types of devices (i.e., not just implantable bands per se). For instance, a syringe and needle may be used to adjust the pressure or amount of fluid within a gastric balloon or other volume occupying device; the pressure or amount of fluid within an infusion port; etc. Thus, targeting apparatuses 305, 405, 505, 605 may be used to assist in finding and/or marking a proper a proper insertion point for a needle to inject fluid into (or withdraw fluid from) such other types of devices. Various other types of devices and systems with which the examples described herein may be used will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A needle targeting apparatus comprising:
   (a) an implantable device, wherein the implantable device comprises an internal control module;
   (b) a sense head, wherein the sense head comprises:
      (i) an external control module including an antenna configured to locate the implantable device, wherein the external control module is operable to communicate with the internal control module, and
      (ii) an annular member defining an opening having a center point and including an inner face facing the central point;
   (c) a guide, wherein the guide is configured to visually indicate a needle insertion point relative to the opening defined by the sense head, wherein the guide comprises a first laser and a second laser disposed on or near the inner face, wherein the first laser and the second laser form an intersecting point positioned within the opening, wherein the intersecting point is proximate to the center point, wherein the first laser and the second laser define a plane within the opening operable to receive a needle transverse to the plane; and
   (d) a laser module operably configured to selectively power the first laser and the second laser, wherein the laser module is operable to vary performance of the first laser and the second laser based on the strength of a signal between the internal control module and external control module.

2. The needle targeting apparatus of claim 1, wherein the guide is removably coupled with the sense head.

3. The needle targeting apparatus of claim 1, wherein the sense head is configured to output visual feedback when the sense head locates an implanted device.

4. The needle targeting apparatus of claim 1, wherein the first laser is substantially perpendicular to the second laser.

5. The needle targeting apparatus of claim 1, further comprising a display operable to provide information to the user.

6. The needle targeting apparatus of claim 5, wherein the information comprises at least one type of information selected from the group consisting of:
   (i) pressure information;
   (ii) location information;
   (iii) orientation information; and
   (iv) signal strength information.

7. A needle targeting apparatus comprising:
   (a) a sense head, wherein the sense head comprises an antenna configured to locate an implanted device, wherein the sense head defines an opening having a center point; and
   (b) a guide, wherein the guide is configured to visually indicate a needle insertion point relative to the opening defined by the sense head, wherein the guide comprises a targeting film, wherein the targeting film comprises:
      (i) a first adhesive portion on one side of the targeting film, wherein the first adhesive is positioned and configured to be removably adhered to the sense head,
      (ii) a second adhesive portion, wherein the second adhesive portion is positioned and configured to adhesively engage a patient's skin on another side of the targeting film,
      (iii) a pull tab for manipulating the guide during use, and
      (iv) a target consisting essentially of a circle in the center of the guide and a single set of crosshairs intersecting the circle and positioned to indicate the center of the circle and the target, wherein the targeting film is configured to cover at least a portion of the opening of the sense head.

8. The needle targeting apparatus of claim 7, wherein the sense head has a paddle-like shape with a graspable handle.

9. The needle targeting apparatus of claim 7, further comprising a control module in communication with the sense head, wherein the control module is operable to determine the position of the sense head in relation to the implanted device.

10. The needle targeting apparatus of claim 9, wherein the control is in communication with an output, wherein the control module is operable to inform the user through the output the closeness of the sense head to the implanted device.

11. The needle targeting apparatus of claim 10, wherein the output comprises a visual display.

* * * * *